United States Patent
Levy

(10) Patent No.: US 10,638,922 B2
(45) Date of Patent: *May 5, 2020

(54) MULTI-CAMERA ENDOSCOPE

(71) Applicant: EndoChoice Innovation Center Ltd., Caesarea (IL)

(72) Inventor: Avi Levy, Herzliya (IL)

(73) Assignee: EndoChoice, Inc., Alpharetta, GA (US)

( * ) Notice: Subject to any disclaimer, the term of this patent is extended or adjusted under 35 U.S.C. 154(b) by 200 days.

This patent is subject to a terminal disclaimer.

(21) Appl. No.: 15/607,941

(22) Filed: May 30, 2017

(65) Prior Publication Data

US 2017/0325672 A1 Nov. 16, 2017

Related U.S. Application Data

(63) Continuation of application No. 14/746,986, filed on Jun. 23, 2015, now Pat. No. 9,706,905, which is a
(Continued)

(51) Int. Cl.
*A61B 1/05* (2006.01)
*A61B 1/015* (2006.01)
(Continued)

(52) U.S. Cl.
CPC .............. *A61B 1/051* (2013.01); *A61B 1/005* (2013.01); *A61B 1/00091* (2013.01);
(Continued)

(58) Field of Classification Search
CPC ......... A61B 1/126; A61B 1/07; A61B 1/0684; A61B 1/0084; A61B 1/018; A61B 1/015;
(Continued)

(56) References Cited

U.S. PATENT DOCUMENTS 4,253,448 A 3/1981 Terada
4,261,345 A 4/1981 Yamaguchi
(Continued)

FOREIGN PATENT DOCUMENTS

CN 1988841 6/2007
CN 101061940 A 10/2007
(Continued)

OTHER PUBLICATIONS

Office Action dated Jan. 15, 2015 for U.S. Appl. No. 13/190,968.
(Continued)

*Primary Examiner* — John P Leubecker

(74) *Attorney, Agent, or Firm* — Bookoff McAndrews, PLLC

(57) ABSTRACT

A tip section of a multi-camera endoscope includes a front-pointing camera on a planar surface of a distal end of the tip section and two side-pointing cameras positioned on a cylindrical surface in proximity to the planar surface such that the side field of view provided by the two side-pointing cameras partially overlaps with the front field of view provided by the front-pointing camera. The tip section further includes a working channel configured for insertion of a surgical tool; and a pathway fluid injector for inflating and/or cleaning a body cavity into which the endoscope is inserted.

9 Claims, 7 Drawing Sheets

Related U.S. Application Data continuation of application No. 13/190,968, filed on Jul. 26, 2011, now Pat. No. 9,101,268, which is a continuation-in-part of application No. 13/119,032, filed as application No. PCT/IL2010/000476 on Jun. 16, 2010, now Pat. No. 9,554,692.

(60) Provisional application No. 61/218,085, filed on Jun. 18, 2009.

(51) Int. Cl.
  *A61B 1/018* (2006.01)
  *A61B 1/00* (2006.01)
  *A61B 1/12* (2006.01)
  *G02B 23/24* (2006.01)
  *A61B 1/06* (2006.01)
  *A61B 1/07* (2006.01)
  *A61B 1/005* (2006.01)

(52) U.S. Cl.
  CPC ...... *A61B 1/00096* (2013.01); *A61B 1/00177* (2013.01); *A61B 1/00181* (2013.01); *A61B 1/015* (2013.01); *A61B 1/018* (2013.01); *A61B 1/0615* (2013.01); *A61B 1/0684* (2013.01); *A61B 1/07* (2013.01); *A61B 1/126* (2013.01); *G02B 23/2423* (2013.01)

(58) Field of Classification Search
  CPC ............ A61B 1/00009; A61B 1/00181; A61B 1/0177; G02B 23/2423
  See application file for complete search history.

(56) References Cited

U.S. PATENT DOCUMENTS

| | | |
|---|---|---|
| 4,402,313 A | 9/1983 | Yabe |
| 4,414,608 A | 11/1983 | Furihata |
| 4,439,030 A | 3/1984 | Ueda |
| 4,469,090 A | 9/1984 | Konomura |
| 4,494,549 A | 1/1985 | Mamba |
| 4,522,196 A | 6/1985 | Cunningham |
| 4,565,423 A | 1/1986 | Ueda |
| 4,576,144 A | 3/1986 | Ishii |
| 4,588,294 A | 5/1986 | Siegmund |
| 4,590,923 A | 5/1986 | Watanabe |
| 4,641,635 A | 2/1987 | Yabe |
| 4,699,463 A | 10/1987 | D'Amelio |
| 4,708,126 A | 11/1987 | Toda |
| 4,736,732 A | 4/1988 | Shimonaka |
| 4,753,222 A | 6/1988 | Morishita |
| 4,764,001 A | 8/1988 | Yokota |
| 4,794,913 A | 1/1989 | Shimonaka |
| 4,801,792 A | 1/1989 | Yamasita |
| 4,841,952 A | 6/1989 | Sato |
| 4,846,154 A | 7/1989 | MacAnally |
| 4,877,314 A | 10/1989 | Kanamori |
| 4,878,485 A | 11/1989 | Adair |
| 4,888,639 A | 12/1989 | Yabe |
| 4,902,115 A | 2/1990 | Takahashi |
| 4,905,670 A | 3/1990 | Adair |
| 4,914,521 A | 4/1990 | Adair |
| 4,974,075 A | 11/1990 | Nakajima |
| 4,976,522 A | 12/1990 | Igarashi |
| 4,982,724 A | 1/1991 | Saito |
| 4,984,878 A | 1/1991 | Miyano |
| 4,998,182 A | 3/1991 | Krauter |
| 5,166,787 A | 11/1992 | Irion |
| 5,193,525 A | 3/1993 | Silverstein |
| 5,239,983 A | 8/1993 | Katsurada |
| 5,296,971 A | 3/1994 | Mori |
| 5,299,561 A | 4/1994 | Yoshimoto |
| 5,305,121 A | 4/1994 | Moll |
| 5,309,227 A | 5/1994 | Inoue |
| 5,313,934 A | 5/1994 | Wiita |
| 5,339,800 A | 8/1994 | Wiita |
| 5,359,456 A | 10/1994 | Kikuchi |
| 5,380,049 A | 1/1995 | Smowton |
| 5,398,056 A | 3/1995 | Yabe |
| 5,408,263 A | 4/1995 | Dolidon |
| 5,412,478 A | 5/1995 | Ishihara |
| 5,420,644 A | 5/1995 | Watanabe |
| 5,432,543 A | 7/1995 | Hasegawa |
| 5,436,767 A | 7/1995 | Suzuki |
| 5,447,148 A | 9/1995 | Oneda |
| 5,452,391 A | 9/1995 | Chou |
| 5,460,167 A | 10/1995 | Yabe |
| 5,483,951 A | 1/1996 | Frassica |
| 5,485,316 A | 1/1996 | Mori |
| 5,489,256 A | 2/1996 | Adair |
| 5,507,717 A | 4/1996 | Kura |
| 5,512,940 A | 4/1996 | Takasugi |
| 5,515,449 A | 5/1996 | Tsuruoka |
| 5,518,501 A | 5/1996 | Oneda |
| 5,518,502 A | 5/1996 | Kaplan |
| 5,547,455 A * | 8/1996 | McKenna ............ A61B 1/0005 348/65 |
| 5,547,457 A | 8/1996 | Tsuyuki |
| 5,550,582 A | 8/1996 | Takasugi |
| 5,585,840 A | 12/1996 | Watanabe |
| 5,587,839 A | 12/1996 | Miyano |
| 5,589,874 A | 12/1996 | Buchin |
| 5,592,216 A | 1/1997 | Uehara |
| 5,605,530 A | 2/1997 | Fischell |
| 5,609,560 A | 3/1997 | Ichikawa |
| 5,617,136 A | 4/1997 | Iso |
| 5,630,782 A | 5/1997 | Adair |
| 5,653,677 A | 8/1997 | Okada |
| 5,656,011 A | 8/1997 | Uihlein |
| 5,675,378 A | 10/1997 | Takasugi |
| 5,679,110 A | 10/1997 | Hamazaki |
| 5,685,823 A * | 11/1997 | Ito ..................... A61B 1/00091 600/121 |
| 5,701,155 A | 12/1997 | Wood |
| 5,702,345 A | 12/1997 | Wood |
| 5,702,347 A | 12/1997 | Yabe |
| 5,716,323 A | 2/1998 | Lee |
| 5,725,474 A | 3/1998 | Yasui |
| 5,725,476 A | 3/1998 | Yasui |
| 5,725,477 A | 3/1998 | Yasui |
| 5,728,045 A | 3/1998 | Komi |
| 5,751,340 A | 5/1998 | Strobl |
| 5,764,809 A | 6/1998 | Nomami |
| 5,777,797 A | 7/1998 | Miyano |
| 5,782,751 A | 7/1998 | Matsuno |
| 5,793,539 A | 8/1998 | Konno |
| 5,800,341 A | 9/1998 | McKenna |
| 5,812,187 A | 9/1998 | Watanabe |
| 5,830,124 A | 11/1998 | Suzuki |
| 5,852,511 A | 12/1998 | Tateyama |
| 5,870,234 A | 2/1999 | EbbesmeiemeeSchitthof |
| 5,871,439 A | 2/1999 | Takahashi |
| 5,876,326 A | 3/1999 | Takamura |
| 5,879,284 A | 3/1999 | Tsujita |
| 5,894,322 A | 4/1999 | Hamano |
| 5,912,764 A | 6/1999 | Togino |
| 5,913,817 A | 6/1999 | Lee |
| 5,914,810 A | 6/1999 | Watts |
| 5,916,148 A | 6/1999 | Tsuyuki |
| 5,929,901 A | 7/1999 | Adair |
| 5,930,424 A | 7/1999 | Heimberger |
| 5,933,275 A | 8/1999 | Igarashi |
| 5,933,282 A | 8/1999 | Tomioka |
| 5,936,773 A | 8/1999 | Togino |
| 5,940,126 A * | 8/1999 | Kimura ................ H04N 5/2253 348/294 |
| 5,961,445 A | 10/1999 | Chikama |
| 5,969,888 A | 10/1999 | Sukekawa |
| 5,986,693 A | 11/1999 | Adair |
| 5,989,185 A | 11/1999 | Miyazaki |
| 5,993,037 A | 11/1999 | Tomioka |
| 5,995,136 A | 11/1999 | Hattori |
| 6,009,189 A | 12/1999 | Schaack |
| 6,025,873 A | 2/2000 | Nishioka |

(56) References Cited

U.S. PATENT DOCUMENTS

| | | |
|---|---|---|
| 6,043,839 A | 3/2000 | Adair |
| 6,069,698 A | 5/2000 | Ozawa |
| 6,080,104 A | 6/2000 | Ozawa |
| 6,104,540 A | 8/2000 | Hayakawa |
| 6,110,127 A | 8/2000 | Suzuki |
| 6,124,989 A | 9/2000 | Oode |
| 6,139,175 A | 10/2000 | Tomioka |
| 6,139,490 A | 10/2000 | Breidenthal |
| 6,147,808 A | 11/2000 | Togino |
| 6,163,401 A | 12/2000 | Igarashi |
| 6,166,858 A | 12/2000 | Togino |
| 6,181,481 B1 | 1/2001 | Yamamoto |
| 6,184,923 B1 | 2/2001 | Miyazaki |
| 6,185,046 B1 | 2/2001 | Togino |
| 6,201,646 B1 | 3/2001 | Togino |
| 6,201,648 B1 | 3/2001 | Togino |
| 6,211,904 B1 | 4/2001 | Adair |
| 6,215,517 B1 | 4/2001 | Takahashi |
| 6,217,500 B1 | 4/2001 | Helseth |
| 6,245,086 B1 | 6/2001 | Storz |
| 6,249,391 B1 | 6/2001 | Hayakawa |
| 6,260,994 B1 | 7/2001 | Matsumoto |
| 6,261,226 B1 | 7/2001 | McKenna |
| 6,275,255 B1 | 8/2001 | Adair |
| 6,295,368 B1 | 9/2001 | Hasegawa |
| 6,306,082 B1 | 10/2001 | Takahashi |
| 6,310,642 B1 | 10/2001 | Adair |
| 6,310,736 B1 | 10/2001 | Togino |
| 6,315,712 B1 | 11/2001 | Rovegno |
| 6,322,496 B1 | 11/2001 | Iida |
| 6,327,094 B1 | 12/2001 | Aoki |
| 6,327,101 B1 | 12/2001 | Miyano |
| 6,334,845 B1 | 1/2002 | Higuchi |
| 6,353,504 B1 | 3/2002 | Yamamoto |
| 6,387,045 B1 | 5/2002 | Takahashi |
| 6,398,723 B1 | 6/2002 | Kehr |
| 6,400,514 B2 | 6/2002 | Minami |
| 6,422,995 B2 | 7/2002 | Akiba |
| 6,425,857 B1 | 7/2002 | Rudischhauser |
| 6,450,950 B2 | 9/2002 | Irion |
| 6,461,304 B1 | 10/2002 | Tanaka |
| 6,464,631 B1 | 10/2002 | Girke |
| 6,464,633 B1 | 10/2002 | Hosoda |
| 6,468,201 B1 | 10/2002 | Burdick |
| 6,468,202 B1 | 10/2002 | Irion |
| 6,471,636 B1 | 10/2002 | Sane |
| 6,471,637 B1 | 10/2002 | Green |
| 6,473,116 B1 | 10/2002 | Takahashi |
| 6,476,851 B1 | 11/2002 | Nakamura |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,530,881 B1 | 3/2003 | Ailinger |
| 6,533,722 B2 | 3/2003 | Nakashima |
| 6,545,703 B1 | 4/2003 | Takahashi |
| 6,551,239 B2 | 4/2003 | Renner |
| 6,554,767 B2 | 4/2003 | Tanaka |
| 6,567,114 B2 | 5/2003 | Takahashi |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| 6,618,205 B2 | 9/2003 | Murayama |
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,677,983 B1 | 1/2004 | Takahashi |
| 6,677,984 B2 | 1/2004 | Kobayashi |
| 6,677,992 B1 | 1/2004 | Matsumoto |
| 6,692,430 B2 | 2/2004 | Adler |
| 6,692,431 B2 | 2/2004 | Kazakevich |
| 6,699,181 B2 | 3/2004 | Wako |
| 6,699,185 B2 | 3/2004 | Gminder |
| 6,704,052 B1 | 3/2004 | Togino |
| 6,712,760 B2 | 3/2004 | Sano |
| D490,898 S | 6/2004 | Hayamizu |
| 6,764,439 B2 | 7/2004 | Schaaf |
| 6,778,208 B2 | 8/2004 | Takeshige |
| 6,788,343 B1 | 9/2004 | Togino |
| 6,793,621 B2 | 9/2004 | Butler |
| 6,801,325 B2 | 10/2004 | Farr |
| 6,809,499 B2 | 10/2004 | Solingen |
| 6,809,866 B2 | 10/2004 | Xie |
| 6,829,003 B2 | 12/2004 | Takami |
| 6,832,984 B2 | 12/2004 | Stelzer |
| 6,844,985 B2 | 1/2005 | Murayama |
| 6,846,311 B2 | 1/2005 | Gatto |
| 6,849,043 B2 | 2/2005 | Kondo |
| 6,860,516 B2 | 3/2005 | Ouchi |
| 6,876,380 B2 | 4/2005 | Abe |
| 6,887,194 B2 | 5/2005 | Hart |
| 6,888,119 B2 | 5/2005 | Iizuka |
| 6,898,086 B2 | 5/2005 | Takami |
| 6,899,673 B2 | 5/2005 | Ogura |
| 6,900,829 B1 | 5/2005 | Ozawa |
| 6,900,950 B2 | 5/2005 | Nagata |
| 6,902,529 B2 | 6/2005 | Onishi |
| 6,903,761 B1 | 6/2005 | Abe |
| 6,918,693 B2 | 7/2005 | Ota |
| 6,921,362 B2 | 7/2005 | Ouchi |
| 6,930,705 B2 | 8/2005 | Tanaka |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,086 B2 | 5/2006 | Ozawa |
| 7,074,181 B2 | 7/2006 | Futatsugi |
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |
| 7,180,686 B2 | 2/2007 | Kato |
| 7,218,454 B2 | 5/2007 | Miyano |
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |

(56) References Cited

U.S. PATENT DOCUMENTS

| | | |
|---|---|---|
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |
| 7,542,069 B2 | 6/2009 | Tashiro |
| 7,553,276 B2 | 6/2009 | Iddan |
| 7,559,889 B2 | 7/2009 | Takahashi |
| 7,559,892 B2 | 7/2009 | Adler |
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,630,148 B1 | 12/2009 | Yang |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |
| 7,701,650 B2 | 4/2010 | Lin |
| 7,725,013 B2 | 5/2010 | Sugimoto |
| 7,728,867 B2 | 6/2010 | Fukuyama |
| 7,734,160 B2 | 6/2010 | Sudo |
| 7,746,566 B2 | 6/2010 | Mizusawa |
| 7,746,572 B2 | 6/2010 | Asami |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,772,786 B2 | 8/2010 | Hosoda |
| 7,773,110 B2 | 8/2010 | Abe |
| 7,773,122 B2 | 8/2010 | Irion |
| 7,773,318 B2 | 8/2010 | Takato |
| 7,775,971 B2 | 8/2010 | Fujimori |
| 7,775,973 B2 | 8/2010 | Okada |
| 7,789,822 B2 | 9/2010 | Suzuki |
| 7,800,656 B2 | 9/2010 | Takeuchi |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,852,513 B2 | 12/2010 | Donomae |
| 7,893,956 B2 | 2/2011 | Ayrenschmalz |
| 7,896,802 B2 | 3/2011 | Otawara |
| 7,901,352 B2 | 3/2011 | Minami |
| 7,907,168 B2 | 3/2011 | Eino |
| 7,907,170 B2 | 3/2011 | Watanabe |
| 7,907,352 B2 | 3/2011 | Miyano |
| 7,914,443 B2 | 3/2011 | Uchimura |
| 7,918,788 B2 | 4/2011 | Lin |
| 7,938,773 B2 | 5/2011 | Kawai |
| 7,940,296 B2 | 5/2011 | Ogino |
| 7,942,814 B2 | 5/2011 | Remijan |
| 7,951,068 B2 | 5/2011 | Kura |
| 7,967,745 B2 | 6/2011 | Gilad |
| 7,976,462 B2 * | 7/2011 | Wright ............... A61B 1/00096 600/171 |
| 7,995,093 B2 | 8/2011 | Takeuchi |
| 7,998,064 B2 | 8/2011 | Otawara |
| 8,002,696 B2 | 8/2011 | Suzuki |
| 8,027,101 B2 | 9/2011 | Suda |
| 8,033,992 B2 | 10/2011 | Hino |
| 8,035,684 B2 | 10/2011 | Wakito |
| 8,038,600 B2 | 10/2011 | Uchiyama |
| 8,043,207 B2 | 10/2011 | Adams |
| 8,060,172 B2 | 11/2011 | Ishihara |
| 8,063,962 B2 | 11/2011 | Hagihara |
| 8,066,631 B2 | 11/2011 | Wimmer |
| 8,072,483 B2 | 12/2011 | Tomioka |
| 8,072,537 B2 | 12/2011 | Schwarz |
| 8,072,693 B2 | 12/2011 | Togino |
| 8,075,477 B2 | 12/2011 | Nakamura |
| 8,075,478 B2 | 12/2011 | Campos |
| 8,098,441 B2 | 1/2012 | Sasamoto |
| 8,100,920 B2 | 1/2012 | Gambale |
| 8,102,415 B2 | 1/2012 | Iriyama |
| 8,105,233 B2 | 1/2012 | AbouElKheir |
| 8,113,846 B2 | 2/2012 | Wallaker |
| 8,125,514 B2 | 2/2012 | Sekiguchi |
| 8,125,515 B2 | 2/2012 | Hibi |
| 8,130,454 B2 | 3/2012 | Noguchi |
| 8,135,192 B2 | 3/2012 | Matsuzaki |
| 8,135,454 B2 | 3/2012 | Daniels |
| 8,139,296 B2 | 3/2012 | Ito |
| 8,144,191 B2 | 3/2012 | Kawanishi |
| 8,149,274 B2 | 4/2012 | Yamazaki |
| 8,152,718 B2 | 4/2012 | Cheng |
| 8,152,821 B2 | 4/2012 | Gambale |
| 8,157,798 B2 | 4/2012 | Takahashi |
| 8,164,836 B2 | 4/2012 | Uzawa |
| 8,167,791 B2 | 5/2012 | Tanaka |
| 8,167,795 B2 | 5/2012 | Hoeg |
| 8,167,796 B2 | 5/2012 | Negishi |
| 8,182,419 B2 | 5/2012 | Kohno |
| 8,187,171 B2 | 5/2012 | Irion |
| 8,187,174 B2 | 5/2012 | Wang |
| 8,189,041 B2 | 5/2012 | Konishi |
| 8,189,062 B2 | 5/2012 | Irion |
| 8,194,380 B2 | 6/2012 | Murata |
| 8,197,400 B2 | 6/2012 | Boutillette |
| 8,200,042 B2 | 6/2012 | Doi |
| 8,208,015 B2 | 6/2012 | Unsai |
| 8,211,009 B2 | 7/2012 | Tanaka |
| 8,212,862 B2 | 7/2012 | Kase |
| 8,212,863 B2 | 7/2012 | Tanaka |
| 8,221,309 B2 | 7/2012 | Iida |
| 8,221,311 B2 | 7/2012 | Campos |

(56) References Cited

U.S. PATENT DOCUMENTS

| | | | |
|---|---|---|---|
| 8,223,198 B2 | 7/2012 | Shibasaki |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,565 B2 | 9/2012 | Okada |
| 8,279,275 B2 | 10/2012 | Gono |
| 8,295,566 B2 | 10/2012 | Nishimura |
| 8,300,325 B2 | 10/2012 | Katahira |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyamoto |
| 8,444,548 B2 | 5/2013 | Kumei |
| 8,449,456 B2 | 5/2013 | Ueno |
| 8,449,457 B2 | 5/2013 | Aizenfeld |
| 8,456,562 B2 | 6/2013 | Ishii |
| 8,460,182 B2 | 6/2013 | Ouyang |
| 8,465,421 B2 | 6/2013 | Finkman |
| 8,480,670 B2 | 7/2013 | Sugita |
| 8,491,467 B2 | 7/2013 | Miyamoto |
| 8,520,919 B2 | 8/2013 | Stepp |
| 8,523,764 B2 | 9/2013 | Hatcher |
| 8,523,766 B2 | 9/2013 | Kudoh |
| 9,101,268 B2 * | 8/2015 | Levy | A61B 1/00177 |
| 9,492,063 B2 * | 11/2016 | Levy | A61B 1/00181 |
| 9,554,692 B2 * | 1/2017 | Levy | A61B 1/00091 |
| 9,706,905 B2 * | 7/2017 | Levy | A61B 1/00177 |
| 2002/0007110 A1 * | 1/2002 | Irion | A61B 1/00181 |
| | | | 600/170 |
| 2002/0087047 A1 | 7/2002 | Remijan |
| 2002/0098732 A1 | 7/2002 | Shimizu |
| 2002/0109774 A1 * | 8/2002 | Meron | A61B 1/00096 |
| | | | 348/74 |
| 2002/0151768 A1 | 10/2002 | Akiba |
| 2002/0161281 A1 | 10/2002 | Jaffe |
| 2002/0161282 A1 | 10/2002 | Fulghum |
| 2002/0183591 A1 | 12/2002 | Matsuura |
| 2003/0030918 A1 | 2/2003 | Murayama |
| 2003/0032860 A1 | 2/2003 | Avni |
| 2003/0036681 A1 | 2/2003 | Aviv |
| 2003/0055314 A1 | 3/2003 | Petitto |
| 2003/0083552 A1 | 5/2003 | Remijan |
| 2003/0125788 A1 | 7/2003 | Long |
| 2003/0130564 A1 | 7/2003 | Martone |
| 2003/0139648 A1 | 7/2003 | Foley |
| 2003/0158462 A1 | 8/2003 | Takase |
| 2003/0181787 A1 | 9/2003 | Kondo |
| 2003/0199860 A1 | 10/2003 | Loeb |
| 2004/0015049 A1 | 1/2004 | Zaar |
| 2004/0019347 A1 | 1/2004 | Sakurai |
| 2004/0024290 A1 | 2/2004 | Root |
| 2004/0034311 A1 | 2/2004 | Mihalcik |
| 2004/0073120 A1 | 4/2004 | Motz |
| 2004/0104999 A1 | 6/2004 | Okada |
| 2004/0111012 A1 | 6/2004 | Whitman |
| 2004/0122290 A1 * | 6/2004 | Irion | A61B 1/00181 |
| | | | 600/171 |
| 2004/0133076 A1 | 7/2004 | Kobayashi |
| 2004/0138532 A1 | 7/2004 | Glukhovsky |
| 2004/0143162 A1 | 7/2004 | Krattiger |
| 2004/0158129 A1 | 8/2004 | Okada |
| 2004/0160682 A1 | 8/2004 | Miyano |
| 2004/0176661 A1 | 9/2004 | Futatsugi |
| 2004/0190159 A1 | 9/2004 | Hasegawa |
| 2004/0210113 A1 | 10/2004 | Hasegawa |
| 2004/0220451 A1 | 11/2004 | Gravenstein |
| 2004/0242958 A1 | 12/2004 | Fujikawa |
| 2004/0242961 A1 | 12/2004 | Bughici |
| 2004/0249247 A1 | 12/2004 | Iddan |
| 2004/0254423 A1 | 12/2004 | Wendlandt |
| 2004/0267093 A1 | 12/2004 | Miyagi |
| 2005/0020876 A1 | 1/2005 | Shioda |
| 2005/0027164 A1 | 2/2005 | Barbato |
| 2005/0038317 A1 * | 2/2005 | Ratnakar | A61B 1/00105 |
| | | | 600/101 |
| 2005/0038318 A1 | 2/2005 | Goldwasser |
| 2005/0043583 A1 | 2/2005 | Killmann |
| 2005/0080342 A1 | 4/2005 | Gilreath |
| 2005/0090709 A1 | 4/2005 | Okada |
| 2005/0096501 A1 | 5/2005 | Stelzer |
| 2005/0154255 A1 | 7/2005 | Jacobs |
| 2005/0154262 A1 | 7/2005 | Banik |
| 2005/0182295 A1 | 8/2005 | Soper |
| 2005/0203338 A1 | 9/2005 | Couvillon |
| 2005/0234296 A1 | 10/2005 | Saadat |
| 2005/0234347 A1 | 10/2005 | Yamataka |
| 2005/0251127 A1 | 11/2005 | Brosch |
| 2005/0256376 A1 | 11/2005 | Bar-Or |
| 2005/0261553 A1 | 11/2005 | Swain |
| 2005/0272975 A1 | 12/2005 | McWeeney |
| 2005/0283048 A1 | 12/2005 | Gill |
| 2005/0284491 A1 | 12/2005 | Tashiro |
| 2006/0047184 A1 | 3/2006 | Banik |
| 2006/0052663 A1 | 3/2006 | Koitabashi |
| 2006/0063976 A1 | 3/2006 | Aizenfeld |
| 2006/0069307 A1 | 3/2006 | Boulais |
| 2006/0069314 A1 | 3/2006 | Farr |
| 2006/0149129 A1 | 7/2006 | Watts |
| 2006/0173244 A1 | 8/2006 | Boulais |
| 2006/0183971 A1 | 8/2006 | Haviv |
| 2006/0183975 A1 | 8/2006 | Saadat |
| 2006/0189845 A1 | 8/2006 | Maahs |
| 2006/0211914 A1 | 9/2006 | Kasahara |
| 2006/0217594 A1 | 9/2006 | Ferguson |
| 2006/0224040 A1 | 10/2006 | Khait |
| 2006/0229499 A1 | 10/2006 | Eisenkolb |
| 2006/0241347 A1 | 10/2006 | Whitehead |
| 2006/0252994 A1 * | 11/2006 | Ratnakar | A61B 1/00179 |
| | | | 600/173 |
| 2006/0264704 A1 | 11/2006 | Fujimori |
| 2006/0293556 A1 | 12/2006 | Garner |
| 2006/0293562 A1 | 12/2006 | Uchimura |
| 2007/0015964 A1 | 1/2007 | Eversull |
| 2007/0015968 A1 | 1/2007 | Shelnutt |
| 2007/0019916 A1 | 1/2007 | Takami |
| 2007/0020694 A1 | 1/2007 | Pickford |
| 2007/0049803 A1 | 3/2007 | Moriyama |
| 2007/0055100 A1 | 3/2007 | Kato |
| 2007/0073109 A1 | 3/2007 | Irion |
| 2007/0078304 A1 | 4/2007 | Shimizu |
| 2007/0083081 A1 | 4/2007 | Schlagenhauf |
| 2007/0100206 A1 | 5/2007 | Lin |
| 2007/0106119 A1 | 5/2007 | Hirata |
| 2007/0115376 A1 | 5/2007 | Igarashi |
| 2007/0118019 A1 | 5/2007 | Mitani |
| 2007/0123748 A1 | 5/2007 | Meglan |
| 2007/0142711 A1 | 6/2007 | Bayer |
| 2007/0162095 A1 | 7/2007 | Kimmel |
| 2007/0167673 A1 | 7/2007 | Enomoto |
| 2007/0167681 A1 | 7/2007 | Gill |
| 2007/0173686 A1 | 7/2007 | Lin |
| 2007/0173687 A1 | 7/2007 | Shima |
| 2007/0177008 A1 | 8/2007 | Bayer |
| 2007/0177009 A1 | 8/2007 | Bayer |
| 2007/0185384 A1 * | 8/2007 | Bayer | A61B 1/00174 |
| | | | 600/129 |
| 2007/0197875 A1 * | 8/2007 | Osaka | A61B 1/00096 |
| | | | 600/173 |
| 2007/0203396 A1 * | 8/2007 | McCutcheon | A61B 1/00082 |
| | | | 600/173 |
| 2007/0206945 A1 | 9/2007 | Delorme |
| 2007/0208225 A1 | 9/2007 | Czaniera |
| 2007/0213590 A1 | 9/2007 | Squicciarini |

(56) References Cited

U.S. PATENT DOCUMENTS

| | | |
|---|---|---|
| 2007/0213591 A1 | 9/2007 | Aizenfeld |
| 2007/0225556 A1 | 9/2007 | Ortiz |
| 2007/0225565 A1 | 9/2007 | Ogino |
| 2007/0229656 A1 | 10/2007 | Khait |
| 2007/0244353 A1 | 10/2007 | Larsen |
| 2007/0244362 A1 | 10/2007 | El-Hachem |
| 2007/0244366 A1 | 10/2007 | Murata |
| 2007/0249899 A1 | 10/2007 | Seifert |
| 2007/0265498 A1 | 11/2007 | Ito |
| 2007/0282165 A1 | 12/2007 | Hopkins |
| 2007/0293720 A1 | 12/2007 | Bayer |
| 2008/0009672 A1 | 1/2008 | Krattiger |
| 2008/0021274 A1 | 1/2008 | Bayer |
| 2008/0021281 A1 | 1/2008 | Fujimori |
| 2008/0039689 A1 | 2/2008 | Yoshimitsu |
| 2008/0039693 A1 | 2/2008 | Karasawa |
| 2008/0045797 A1 | 2/2008 | Yasushi |
| 2008/0051628 A1 | 2/2008 | Pecherer |
| 2008/0051629 A1 | 2/2008 | Sugiyama |
| 2008/0051655 A1 | 2/2008 | Sato |
| 2008/0058595 A1 | 3/2008 | Snoke |
| 2008/0058598 A1 | 3/2008 | Ries |
| 2008/0058601 A1 | 3/2008 | Fujimori |
| 2008/0064931 A1 | 3/2008 | Schena |
| 2008/0065127 A1 | 3/2008 | Adams |
| 2008/0071290 A1 | 3/2008 | Larkin |
| 2008/0100699 A1 | 5/2008 | Hibi |
| 2008/0130108 A1 | 6/2008 | Bayer |
| 2008/0139881 A1 | 6/2008 | Cover |
| 2008/0167529 A1 | 7/2008 | Otawara |
| 2008/0171910 A1 | 7/2008 | Kanazawa |
| 2008/0177139 A1 | 7/2008 | Courtney |
| 2008/0177140 A1 | 7/2008 | Cline |
| 2008/0221388 A1 | 7/2008 | Courtney |
| 2008/0188715 A1 | 8/2008 | Fujimoto |
| 2008/0225134 A1 | 9/2008 | Amling |
| 2008/0255425 A1 | 10/2008 | Voegele |
| 2008/0262302 A1 | 10/2008 | Azarbarzin |
| 2008/0262312 A1 | 10/2008 | Carroll |
| 2008/0312497 A1 | 12/2008 | Elmouelhi |
| 2009/0054790 A1 | 2/2009 | Czaniera |
| 2009/0062615 A1 | 3/2009 | Yamaya |
| 2009/0086017 A1 | 4/2009 | Miyano |
| 2009/0093679 A1 | 4/2009 | Suigetsu |
| 2009/0118577 A9 | 5/2009 | Snay |
| 2009/0137869 A1 | 5/2009 | Soutorine |
| 2009/0147076 A1 | 6/2009 | Ertas |
| 2009/0161234 A1 | 6/2009 | Sasamoto |
| 2009/0163769 A1 | 6/2009 | Robertson |
| 2009/0209811 A1 | 8/2009 | Higuchi |
| 2009/0216084 A1 | 8/2009 | Yamane |
| 2009/0231419 A1 | 9/2009 | Bayer |
| 2009/0247831 A1 | 10/2009 | Miyamoto |
| 2009/0253966 A1 | 10/2009 | Ichimura |
| 2009/0259097 A1 | 10/2009 | Thompson |
| 2009/0259102 A1 | 10/2009 | Koninckx |
| 2009/0268011 A1 | 10/2009 | Scott |
| 2009/0284649 A1 | 11/2009 | Pease |
| 2009/0287047 A1 | 11/2009 | Onoda |
| 2009/0287192 A1 | 11/2009 | Vivenzio |
| 2009/0290236 A1 | 11/2009 | Wang |
| 2009/0306474 A1 | 12/2009 | Wilson |
| 2009/0306476 A1 | 12/2009 | Banik |
| 2009/0318757 A1 | 12/2009 | Singh |
| 2009/0326321 A1* | 12/2009 | Jacobsen ............ A61B 1/00177 600/109 |
| 2010/0010301 A1 | 1/2010 | Hale |
| 2010/0010302 A1 | 1/2010 | Hadani |
| 2010/0013914 A1* | 1/2010 | Bettesh ............ A61B 1/00016 348/77 |
| 2010/0016673 A1 | 1/2010 | Bandy |
| 2010/0030020 A1 | 2/2010 | Sanders |
| 2010/0042097 A1 | 2/2010 | Newton |
| 2010/0047733 A1 | 2/2010 | Nahlieli |
| 2010/0053312 A1 | 3/2010 | Watanabe |
| 2010/0073470 A1 | 3/2010 | Takasaki |
| 2010/0076268 A1 | 3/2010 | Takasugi |
| 2010/0081874 A1 | 4/2010 | Miyamoto |
| 2010/0081875 A1 | 4/2010 | Fowler |
| 2010/0087706 A1 | 4/2010 | Syed |
| 2010/0121142 A1 | 5/2010 | Ouyang |
| 2010/0123950 A1 | 5/2010 | Fujiwara |
| 2010/0130822 A1 | 5/2010 | Katayama |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Diaki |
| 2010/0245653 A1 | 9/2010 | Bodor |
| 2010/0249496 A1 | 9/2010 | Cardenas |
| 2010/0256447 A1 | 10/2010 | Dubi |
| 2010/0286475 A1 | 11/2010 | Robertson |
| 2010/0296178 A1 | 11/2010 | Genet |
| 2010/0298640 A1 | 11/2010 | Oneda |
| 2010/0298773 A1 | 11/2010 | Nitsan |
| 2010/0305503 A1 | 12/2010 | Fang |
| 2010/0317919 A1 | 12/2010 | Takaoka |
| 2010/0317921 A1 | 12/2010 | Marple |
| 2010/0318061 A1 | 12/2010 | Derrick |
| 2011/0028790 A1 | 2/2011 | Farr |
| 2011/0054256 A1 | 3/2011 | Cushner |
| 2011/0112363 A1 | 5/2011 | Koga |
| 2011/0160530 A1 | 6/2011 | Ratnakar |
| 2011/0169931 A1 | 7/2011 | Pascal |
| 2011/0184243 A1 | 7/2011 | Wright |
| 2011/0196200 A1 | 8/2011 | Glozman |
| 2011/0196204 A1 | 8/2011 | Setty |
| 2011/0211267 A1 | 9/2011 | Takato |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1 | 11/2011 | Gellman |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0057251 A1 | 3/2012 | Takato |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0095391 A1 | 4/2012 | Bendele |
| 2012/0104230 A1 | 5/2012 | Eismann |
| 2012/0178995 A1 | 7/2012 | Newton |
| 2012/0209062 A1 | 8/2012 | Qiao |
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0253121 A1 | 10/2012 | Kitano |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |

(56) References Cited

U.S. PATENT DOCUMENTS

| | | | |
|---|---|---|---|
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0137930 A1 | 5/2013 | Menabde |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0253272 A1 | 9/2013 | Takahashi |
| 2013/0296649 A1 | 11/2013 | Kirma |
| 2013/0314521 A1 | 11/2013 | Satake |
| 2013/0317295 A1 | 11/2013 | Morse |
| 2014/0364691 A1 | 12/2014 | Krivopisk |

FOREIGN PATENT DOCUMENTS

| | | |
|---|---|---|
| CN | 201108422 Y | 9/2008 |
| CN | 4445647 | 4/2009 |
| CN | 101396258 | 4/2009 |
| CN | 101061940 | 6/2011 |
| DE | 102005008153 A1 | 11/2005 |
| EP | 0029555 A2 | 6/1981 |
| EP | 543738 A1 | 5/1993 |
| EP | 730844 | 9/1996 |
| EP | 1195630 A2 | 4/2002 |
| EP | 1325458 | 7/2003 |
| EP | 1347702 A2 | 10/2003 |
| EP | 948283 B1 | 4/2004 |
| EP | 1535565 | 6/2005 |
| EP | 1073365 B1 | 7/2005 |
| EP | 1627595 A1 | 2/2006 |
| EP | 568738 B1 | 6/2006 |
| EP | 1685790 A1 | 8/2006 |
| EP | 1472972 B1 | 10/2006 |
| EP | 1790280 A1 | 5/2007 |
| EP | 1834572 A1 | 9/2007 |
| EP | 1952750 | 8/2008 |
| EP | 1977675 | 10/2008 |
| EP | 1977682 A2 | 10/2008 |
| EP | 1974000653 | 10/2008 |
| EP | 1992292 A1 | 11/2008 |
| EP | 2022389 A1 | 2/2009 |
| EP | 2144571 A2 | 1/2010 |
| EP | 2276389 A1 | 1/2011 |
| EP | 1835847 B1 | 5/2011 |
| EP | 1870014 B1 | 1/2012 |
| EP | 2501271 A1 | 9/2012 |
| EP | 2503933 A1 | 10/2012 |
| EP | 2512577 A2 | 10/2012 |
| EP | 2529660 A1 | 12/2012 |
| EP | 2596756 A1 | 5/2013 |
| EP | 2623019 A1 | 8/2013 |
| GB | 2352922 A | 2/2001 |
| JP | 2010279539 | 12/1920 |
| JP | 55078932 | 6/1980 |
| JP | 51055657 | 11/1986 |
| JP | 5049000594 | 3/1993 |
| JP | 5105000800 | 4/1994 |
| JP | 1000000352 | 1/1995 |
| JP | 8122000657 | 5/1996 |
| JP | 1013007179 | 4/1998 |
| JP | 1015001113 | 6/1998 |
| JP | 11137512 | 5/1999 |
| JP | H11125773 | 5/1999 |
| JP | 1116009340 | 6/1999 |
| JP | 1116009341 | 6/1999 |
| JP | 2000171727 A | 6/2000 |
| JP | 2000325306 | 11/2000 |
| JP | 2001061762 | 3/2001 |
| JP | 2001198086 | 7/2001 |
| JP | 2002000559 | 1/2002 |
| JP | 2002058636 | 2/2002 |
| JP | 2002065575 | 3/2002 |
| JP | 2002078675 | 3/2002 |
| JP | 2002216902 | 8/2002 |
| JP | 2003038431 | 2/2003 |
| JP | 2003061900 | 3/2003 |
| JP | 2003111724 | 4/2003 |
| JP | 2003190082 | 7/2003 |
| JP | 2003220017 | 8/2003 |
| JP | 2003245247 | 9/2003 |
| JP | 2004022391 | 1/2004 |
| JP | 2004049754 | 2/2004 |
| JP | 2004049756 | 2/2004 |
| JP | 2004129834 | 4/2004 |
| JP | 2005013557 A | 1/2005 |
| JP | 2005058547 | 3/2005 |
| JP | 2005253543 | 9/2005 |
| JP | 3765500 | 2/2006 |
| JP | 2006068109 A | 3/2006 |
| JP | 2006218155 | 8/2006 |
| JP | 2007020866 A | 2/2007 |
| JP | 2007185276 | 7/2007 |
| JP | 2008161569 A | 7/2008 |
| JP | 2008229204 | 10/2008 |
| JP | 2009233186 | 10/2009 |
| JP | 2010178766 A | 8/2010 |
| WO | 9219148 A1 | 11/1992 |
| WO | 00052643 A1 | 9/2000 |
| WO | 2002045595 | 6/2002 |
| WO | 2004026125 | 4/2004 |
| WO | 2005082228 A1 | 9/2005 |
| WO | 2006073581 | 7/2006 |
| WO | 2006105932 A1 | 10/2006 |
| WO | 2007113801 A2 | 10/2007 |
| WO | 2007136859 A2 | 11/2007 |
| WO | 2008012813 A1 | 1/2008 |
| WO | 2008073243 | 6/2008 |
| WO | 2008093288 | 8/2008 |
| WO | 2008139770 | 11/2008 |
| WO | 2008155776 | 12/2008 |
| WO | 2008156623 | 12/2008 |
| WO | 2009009414 | 1/2009 |
| WO | 2009025843 | 2/2009 |
| WO | 2009040744 | 4/2009 |
| WO | 2009095915 | 8/2009 |
| WO | 2010028612 | 3/2010 |
| WO | 2010045406 | 4/2010 |
| WO | 2010066788 | 6/2010 |
| WO | 2010146587 A1 | 12/2010 |
| WO | 2011008922 | 1/2011 |
| WO | 2011041724 | 4/2011 |
| WO | 2011083451 | 7/2011 |
| WO | 2011126812 | 10/2011 |
| WO | 2012038958 | 3/2012 |
| WO | 2013131578 | 3/2012 |
| WO | 2012056453 A2 | 5/2012 |
| WO | 2012077116 | 6/2012 |
| WO | 2012077117 A1 | 6/2012 |
| WO | 2012088201 A2 | 6/2012 |
| WO | 2012103266 | 8/2012 |
| WO | 2012120507 A1 | 9/2012 |
| WO | 2012153324 | 11/2012 |
| WO | 2013014673 | 1/2013 |
| WO | 2013024476 | 2/2013 |
| WO | 2013043704 | 3/2013 |
| WO | 2013128136 | 9/2013 |
| WO | 2013144944 | 10/2013 |
| WO | 2014061023 | 4/2014 |

OTHER PUBLICATIONS

Office Action dated Jun. 3, 2015 for U.S. Appl. No. 13/992,014.
Office Action dated May 1, 2015 for U.S. Appl. No. 13/992,021.
First Office Action for CN 2012800171292, dated Feb. 28, 2015.

(56) References Cited

OTHER PUBLICATIONS

Office Action dated Mar. 12, 2015 for U.S. Appl. No. 13/822,908.
Office Action dated Feb. 13, 2015 for U.S. Appl. No. 13/713,449.
Office Action dated Feb. 17, 2015 for U.S. Appl. No. 13/882,004.
Office Action dated Mar. 6, 2015 for U.S. Appl. No. 13/413,059.
Office Action dated Nov. 26, 2014 for U.S. Appl. No. 13/713,466.
Office Action dated Aug. 19, 2015 for U.S. Appl. No. 13/713,466.
Office Action dated Jul. 21, 2015 for U.S. Appl. No. 13/992,021.
Office Action dated Aug. 5, 2015 for U.S. Appl. No. 13/212,627.
First Office Action for CN 2012800368972, dated Jun. 1, 2015.
Office Action for Chinese Patent Application No. 201180067259.2, dated May 29, 2015.
Office Action dated Aug. 4, 2015 for U.S. Appl. No. 13/557,114.
Office Action dated Aug. 6, 2015 for U.S. Appl. No. 13/119,032.
Office Action dated Aug. 27, 2015 for U.S. Appl. No. 13/655,120.
Office Action dated Aug. 19, 2015 for U.S. Appl. No. 13/713,449.
First office action for CN2011800627366, dated Feb. 25, 2015.
Brochure for US Endoscopy's AquaShield Water Bottle System, 2010.
First Image of an Endo Smart Cap, made by Medivators, and obtained from http://www.bymemedical.com/prod/145L. ipg and advertised at http://www.medivators.com/products/endoscopy-procedure-products/irrigation-tubing/endo-smartcap%C2%AE.
International Search Report for PCT/EP2009/066726, dated Aug. 16, 2010.
International Search Report for PCT/IL2011/000832, dated May 16, 2012.
International Search Report for PCT/IL2011/050049, dated May 15, 2012.
International Search Report for PCT/IL2011/050050, dated May 16, 2012.
International Search Report for PCT/IL2012/050037, dated Jun. 1, 2012.
International Search Report for PCT/IL2012/050274, dated Nov. 15, 2012.
International Search Report for PCT/IL2012/050299, dated Nov. 15, 2012.
International Search Report for PCT/IL2013/050840, dated Feb. 2, 2014.
International Search Report of PCT/IL10/00476 dated Sep. 27, 2010, 2 pages.
International Search Report of PCT/IL2011/000745, dated May 8, 2012.
Notice of Allowance dated Jun. 8, 2015 for U.S. Appl. No. 13/984,028.
Notice of Allowance dated Jun. 8, 2015 for U.S. Appl. No. 13/413,252.
Prosecution File History for U.S. Appl. No. 13/190,968; Jul. 26, 2011 through Jun. 17, 2015.
Notice of Allowance dated Jun. 17, 2015 for U.S. Appl. No. 13/190,968.
Supplementary European Search Report for European Application No. EP12823972, dated May 13, 2015.
Extended European Search Report for EP14186113.8, dated Apr. 1, 2015.
Corrected European Search Opinion for EP14186113.8, dated Apr. 29, 2015.
Office Action dated Feb. 9, 2017 for U.S. Appl. No. 14/746,986.
Notice of Allowance dated May 16, 2017 for U.S. Appl. No. 14/746,986.
Supplementary European Search Report for EP13847670, dated May 19, 2016.

* cited by examiner

MULTI-CAMERA ENDOSCOPE

CROSS-REFERENCE TO RELATED APPLICATIONS

This application is a continuation of U.S. patent application Ser. No. 14/746,986, filed Jun. 23, 2015, now U.S. Pat. No. 9,706,905, issued Jul. 18, 2017, which is a continuation of U.S. patent application Ser. No. 13/190,968, filed Jul. 26, 2011, now U.S. Pat. No. 9,101,268, issued Aug. 11, 2015, which is a continuation-in-part (CIP) of U.S. patent application Ser. No. 13/119,032, filed Jul. 15, 2011, now U.S. Pat. No. 9,554,692, issued Jan. 31, 2017, which is a national phase application with the U.S. Patent and Trademark Office of International Patent Application No. PCT/IL2010/000476, filed Jun. 16, 2010, which claims the benefit of U.S. Provisional Patent Application No. 61/218,085, filed Jun. 18, 2009. Each of the above-mentioned applications is herein incorporated by reference in its entirety.

FIELD

Embodiments of the disclosure relate to a multi-camera endoscope.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, according to some embodiments, a tip section of a multi-camera endoscope, the tip section comprising: two or more side-pointing cameras positioned at or in proximity to a distal end of said tip section, wherein the field of view provided by said two or more side-pointing cameras covers a front and side views; one or more discrete illuminator; a working channel configured for insertion of a surgical tool; and a pathway fluid injector for inflating and/or cleaning a body cavity into which the endoscope is inserted.

There is provided, according to some embodiments, a multi-camera endoscope comprising: an elongated shaft terminating with a tip section turnable by way of a bending section, wherein said tip section comprises: two or more side-pointing cameras positioned at or in proximity to a distal end of said tip section, wherein the field of view provided by said two or more side-pointing cameras covers a front and side views; one or more discrete illuminator; a working channel configured for insertion of a surgical tool; and a pathway fluid injector for inflating and/or cleaning a body cavity into which the endoscope is inserted.

There is provided, according to some embodiments, a tip section of a multi-camera endoscope, the tip section comprising: two or more side-pointing cameras positioned at or in proximity to a distal end of said tip section, wherein each of said two or more side-pointing cameras having a discrete illuminator associated therewith, wherein the field of view provided by said two or more side-pointing cameras covers a front and side views; a working channel configured for insertion of a surgical tool; and a pathway fluid injector for inflating and/or cleaning a body cavity into which the endoscope is inserted.

There is provided, according to some embodiments, a multi-camera endoscope comprising: an elongated shaft terminating with a tip section turnable by way of a bending section, wherein said tip section comprises: two or more side-pointing cameras positioned at or in proximity to a distal end of said tip section, wherein each of said two or more side-pointing cameras having a discrete illuminator associated therewith, wherein the field of view provided by said two or more side-pointing cameras covers a front and side views; a working channel configured for insertion of a surgical tool; and a pathway fluid injector for inflating and/or cleaning a body cavity into which the endoscope is inserted.

The tip section may further include two or more side fluid injectors configured for cleaning said two or more side-pointing cameras and/or said discrete side illuminators. The two or more side-pointing cameras may point at directions essentially opposing to one another. The tip section may include three or more side-pointing cameras. According to some embodiments, the three or more side-pointing cameras may be positioned essentially at equal distances from each other along the perimeter of said tip section.

There is provided, according to some embodiments, a tip section of a multi-camera endoscope, the tip section comprising: a front-pointing camera and a discrete front illuminator associated therewith; a front fluid injector configured for cleaning at least one of said front-pointing camera and said discrete front illuminator; a side-pointing camera; a working channel configured for insertion of a surgical tool; and a pathway fluid injector for inflating and/or cleaning a body cavity into which the endoscope is inserted.

There is provided, according to some embodiments, a multi-camera endoscope comprising: an elongated shaft terminating with a tip section turnable by way of a bending section, wherein said tip section comprises: two or more side-pointing cameras positioned at or in proximity to a distal end of said tip section, wherein each of said two or more side-pointing cameras having a discrete illuminator associated therewith, wherein the field of view provided by said two or more side-pointing cameras covers a front and side views; a working channel configured for insertion of a surgical tool; and a pathway fluid injector for inflating and/or cleaning a body cavity into which the endoscope is inserted. The tip section may further include a discrete side illuminator associated with side-pointing camera. The tip section may further include a side fluid injector configured for cleaning said side-pointing camera and/or said discrete side illuminator.

There is provided, according to an embodiment, a multi-camera endoscope comprising: an elongated shaft terminating with a tip section turnable by way of a bending section, wherein said tip section comprises: a front-pointing camera and a discrete front illuminator associated therewith; a front fluid injector configured for cleaning at least one of said front-pointing camera and said discrete front illuminator; a side-pointing camera and a discrete side illuminator associated therewith; a side fluid injector configured for cleaning at least one of said side-pointing camera and said discrete side illuminator; a working channel configured for insertion of a surgical tool; and a pathway fluid injector for inflating and/or cleaning a body cavity into which the endoscope is inserted.

There is further provided, according to an embodiment, a multi-camera endoscopy system comprising: an endoscope comprising a handle and an elongated shaft terminating with a tip section turnable by way of a bending section, wherein said tip section comprises: a front-pointing camera and a discrete front illuminator associated therewith, a front fluid injector configured for cleaning at least one of said front-pointing camera and said discrete front illuminator, a side-pointing camera and a discrete side illuminator associated therewith, a side fluid injector configured for cleaning at least one of said side-pointing camera and said discrete side illuminator, a working channel configured for insertion of a surgical tool, and a pathway fluid injector for inflating and/or cleaning a body cavity into which the endoscope is inserted; a controller connected to said handle of said endoscope by way of a utility cable; and a display connected to said controller and configured to display video streams received from said front and side-pointing cameras.

In some embodiments, said front-pointing camera and said side-pointing camera are pointing at directions essentially perpendicular to one another.

In some embodiments, said front-pointing camera and said side-pointing camera are pointing approximately 100 to 145 degrees relative to one another.

In some embodiments, a center of said side-pointing camera is positioned approximately 7 to 11 millimeters from a distal end of said tip section.

In some embodiments, each of said discrete front and side illuminators comprises a light-emitting diode (LED).

In some embodiments, at least one of said discrete front and side illuminators is configured to emit white light.

In some embodiments, at least one of said discrete front and side illuminators is configured to emit ultraviolet light.

In some embodiments, at least one of said discrete front and side illuminators is configured to emit infrared light.

In some embodiments, at least one of said discrete front and side illuminators is configured to emit near-infrared light.

In some embodiments, said discrete front and side illuminators are configured to emit light in different wavelengths.

In some embodiments, said tip section further comprises an additional discrete front illuminator configured to emit light having a different wavelength than said discrete front illuminator.

In some embodiments, said additional discrete front illuminator and said discrete front illuminator are configured to simultaneously emit light, each at a different wavelength.

In some embodiments, said tip section further comprises an additional discrete side illuminator configured to emit light having a different wavelength than said discrete side illuminator.

In some embodiments, said additional discrete side illuminator and said discrete side illuminator are configured to simultaneously emit light, each at a different wavelength.

In some embodiments, each of said front-pointing camera and said side-pointing camera comprises a Charge Coupled Device (CCD) or a Complementary Metal Oxide Semiconductor (CMOS) image sensor.

In some embodiments, said front and side fluid injectors are connected to a same fluid supply channel.

In some embodiments, said pathway fluid injector is connected to said fluid supply channel, together with said front and side fluid injectors.

In some embodiments, at least one of said front and side-pointing cameras comprises a lens assembly providing a field of view of 90 degrees or more.

In some embodiments, at least one of said front and side-pointing cameras comprises a lens assembly providing a field of view of 120 degrees or more.

In some embodiments, at least one of said front and side-pointing cameras comprises a lens assembly providing a field of view of 150 degrees or more.

In some embodiments, said front-pointing camera comprises a lens assembly providing a focal length of approximately 3-100 millimeters.

In some embodiments, said side-pointing camera comprises a lens assembly providing a focal length of approximately 2-33 millimeters.

In some embodiments, said tip section further comprises an opposite side-pointing camera pointing at a direction essentially opposite to said side-pointing camera.

In some embodiments, said tip section further comprises a perpendicular side-pointing camera pointing at a direction essentially perpendicular to said side-pointing camera.

In some embodiments, said endoscope is a colonoscope.

In some embodiments, fields of view of said front-pointing camera and side-pointing camera are at least partially overlapping, such that an object of interest viewed via said side-pointing camera remains in the field of view of said side-pointing camera while said tip section is being turned towards the object, and at least until the object becomes visible through said front-pointing camera.

In some embodiments, said utility cable comprises: a fluid channel for providing a fluid to at least one of said injectors; a data cable for receiving video signals from said front and side-pointing cameras; and a power cable for providing electrical power to said front and side-pointing cameras and to said discrete front and side illuminators.

In some embodiments, said controller is configured to process and combine video signals received from said front and side-pointing cameras into a single panoramic video view.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

An aspect of some embodiments relates to an endoscope having a tip section equipped with two or more cameras. According to one embodiment, one of the cameras is positioned at a distal end of the tip section and points forward, and the remaining camera(s) is positioned further back in the tip section, and points sideways.

According to another embodiment, one of the cameras is positioned at a distal (front) end surface of the tip section and points forward, and the remaining camera(s) is positioned further back in the tip section, and points sideways.

According to another embodiment, two or more cameras (for example, three, four or more) are positioned in proximity to or at the distal end of the tip section and point sideways such that the field of view provided by the cameras covers a front and side views. Even though in such configuration, according to some embodiments, no camera is positioned at the distal (front) end surface of the tip section (or in other words, no camera is pointing directly forward), still the field of view of the side cameras allows view of the front direction of the tip and accordingly of the endoscope.

This configuration, advantageously, may allow for a higher rate of detection, compared to conventional configurations, of pathological objects that exist in the body cavity in which the endoscope operates.

The cameras and optionally other elements that exist in the tip section (such as a light source, a working channel, a fluid injector and/or the like) are uniquely scaled, configured and packaged so that they fit within the minimalistic space available inside the tip section, while still providing valuable results.

Figure 1:
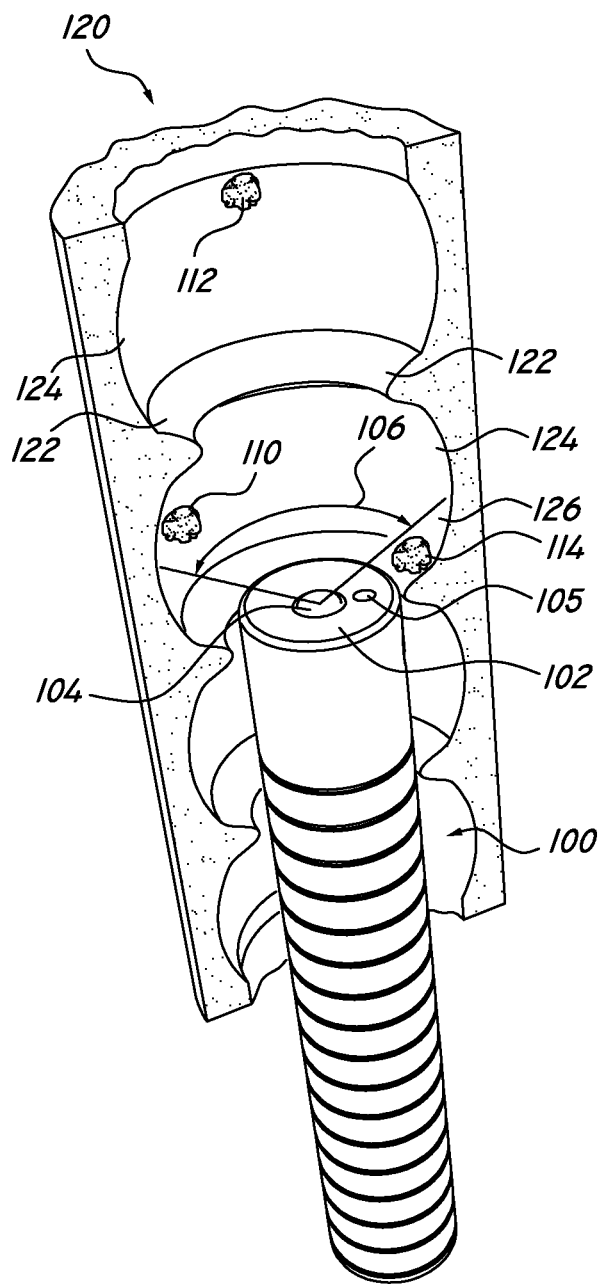
FIG. 1 shows a cross sectional view of a prior art endoscope.

Reference is now made to FIG. 1, which shows a cross sectional view of a prior art endoscope, in this example a colonoscope 100, used within a colon 120 of a patient. The human colon includes a series of annular muscles which appear in this figure as folds 122 protruding from an inner surface 124 of the colon.

Endoscope 100 includes a front-pointing camera 104 positioned at a distal end 102 of the colonoscope. Camera 104 typically has a wide field of view 106. When endoscope 100 is used within a body cavity such as colon 120, the operator advances the endoscope 100 while viewing images (commonly a video feed) transmitted by camera 104. When a polyp, such as polyp 110 or 112 is discovered on a wall of colon 120, the operator may insert a surgical tool (not shown) through a working channel 105 to remove, treat and/or extract a sample of the polyp or its entirety for biopsy.

However, in some cases, a polyp, such as polyp 114 may be located on an inner side of a fold 126, such that it is hidden from the field of view 106 of camera 104. This phenomena is said to greatly contribute to the common statistics, according to which as many as 12-24% of polyps are missed during colonoscopy. Missing polyps, or a "false negative" diagnosis, may result in late discovery of cancer.

Figure 2:
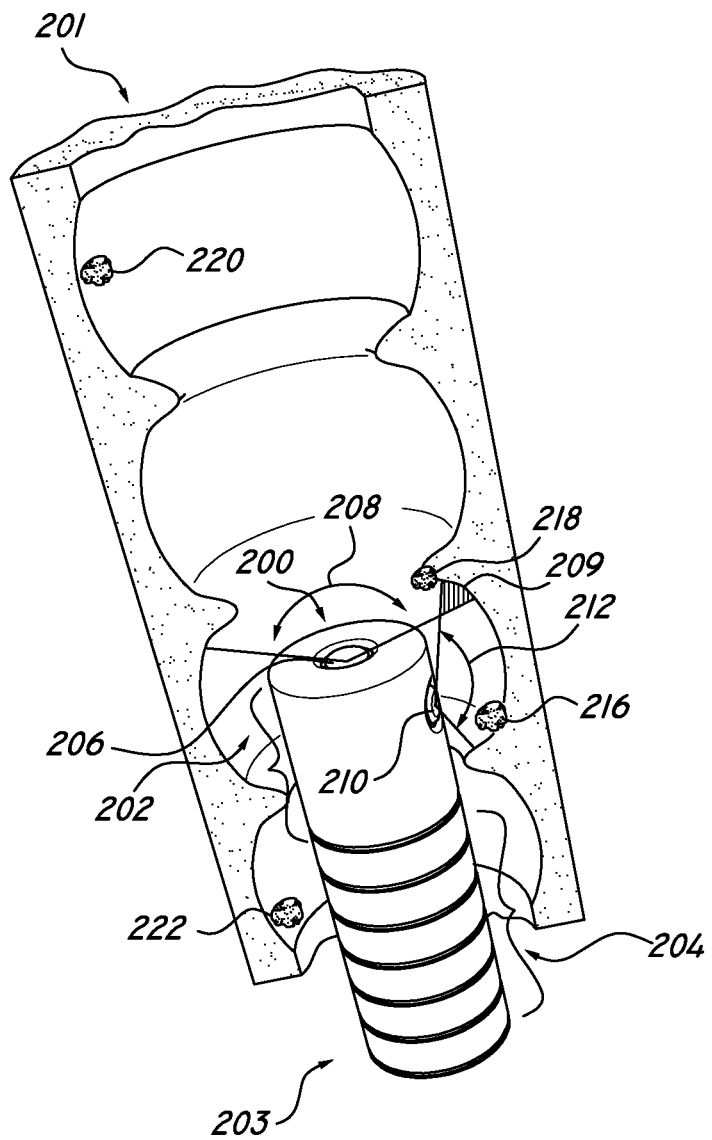
FIG. 2 shows a cross section of a multi-camera endoscope, according to some embodiments.

Reference is now made to FIG. 2, which shows a cross section of a multi-camera endoscope 200, according to an embodiment. Endoscope 200 may include an elongated shaft 203 (not fully shown) terminating with a tip section 202 which is turnable by way of a bending section 204. Advantageously, tip section may include a front-pointing camera 206 as well as a side-pointing camera 210. While front-pointing camera 206 may be able to detect, based on its field of view 208, polyps such as polyps 218 and 220, side-pointing camera 210 may be further able to detect polyps which are normally hidden from the front-pointing camera, such as polyp 216. By rotating endoscope 200 around its longitude, side-pointing camera 210 may detect polyps circumferentially, 360 degrees around the endoscope. This may enable the detection of polyps such as a polyp 222, which is, similar to polyp 216, located on an inner side of a fold. In other configurations (not shown), two or more side-pointing cameras may exist in the tip section, each having a different (or an overlapping, to some degree) field of view.

Advantageously, the fields of view of front-pointing camera 206 and side-pointing camera 210 are at least partially overlapping, such that an object of interest (such as a polyp or another pathology) viewed via the side-pointing camera remains in the field of view of this camera while the tip section is being turned towards the object, and at least until the object becomes visible through the front-pointing camera. This may be beneficial when a polyp is discovered by side-pointing camera 210, and the operator desires to perform a surgical operation on that polyp using a surgical tool inserted through a working channel (not shown in the figure) which has an opening in a distal end surface of tip section 202, next to front-pointing camera 206. For performing the surgical operation, tip section 202 may need to be turned towards the polyp. It may greatly assist the operator if the fields of view of front-pointing camera 206 and side-pointing camera 210 have some overlap, so that the polyp remains in sight throughout the turning of the tip section and the operator does not get disoriented.

Figure 3:
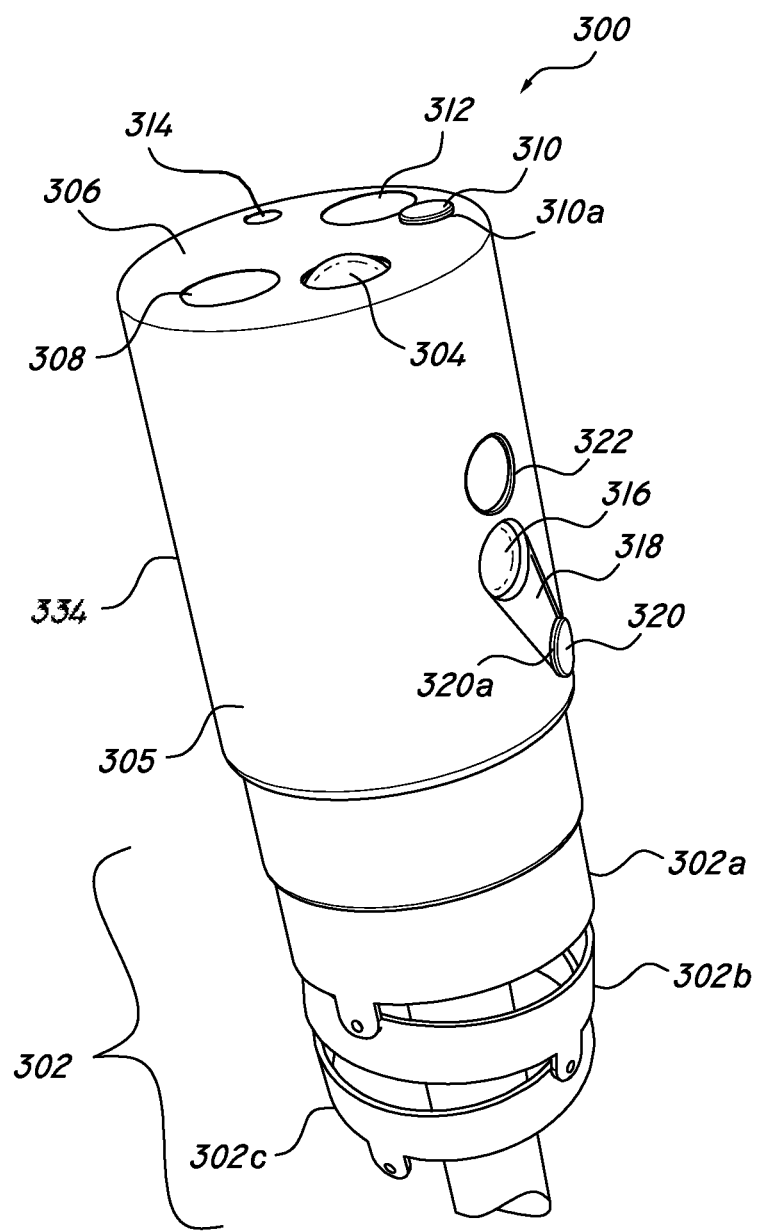
FIG. 3 shows a perspective view of a multi-camera endoscope, according to some embodiments.

Reference is now made to FIG. 3, which shows a perspective view of a multi-camera endoscope 300 in more detail, according to an embodiment. Endoscope 300 may include an elongated shaft (not shown), a bending section (partially shown) 302 and a tip section 334 which terminates the endoscope.

Bending section 302 may include a plurality of links, such as links 302a-c, which enable the turning of tip section 334 in different directions. In a different configuration (not shown), a bending section may be constructed differently, as long as it enables the turning of the tip section 334 in different directions. Bending section 302 may be covered with an elastic sheath (not shown), which may also extend to cover the elongated shaft.

Tip section 334 may include therein a front-pointing camera 304 which may capture images through a hole in a distal end surface 306 of the tip section. A discrete front illuminator 308, which is optionally a light-emitting diode (LED), may be associated with front-pointing camera 304 and used for illuminating its field of view through another hole in distal end surface 306. The LED may be a while light LED, an infrared light LED, a near infrared light LED or an ultraviolet light LED. The term "discrete", in regard to front illuminator 308, may refer to an illumination source which generates light internally—in contrast to a non-discrete illuminator which may be, for example, a fiber optic merely transmitting light generated remotely. In a different configuration (not shown), two or more discrete front illuminators may be present in the tip section, such as for supplying overall stronger illumination and/or for increasing the angular coverage of the illumination. These two or more discrete front illuminators may be located next to one another so that they share a same protective window on the distal end surface of the tip section.

A front fluid injector 310 may be used for cleaning at least one of front-pointing camera 304 and discrete front illuminator 308. Front fluid injector 310 may be slightly elevated from distal end surface 306, to enable it to inject fluid, from its side 310a, onto front-pointing camera 304 and discrete front illuminator 308. Front fluid injector 310 may be configured to inject fluids such as water, air and/or the like.

Distal end surface 306 may further include a hole defining a working channel 312. Working channel 312 may be a hollow tube configured for insertion of a surgical tool to operate on various tissues. For example, miniature forceps may be inserted through working channel 312 in order to remove a polyp or sample of which for biopsy.

A pathway fluid injector 314, defined by another hole in distal end surface 306, may be used for inflating and/or cleaning the body cavity into which endoscope 300 is inserted. Inflation may be performed by flowing air or another gas through pathway fluid injector 314, and may be beneficial for cases in which the body cavity, such as the colon, is shriveled or otherwise does not allow for efficient inspection. Cleaning may be achieved, for example, by injecting a liquid, such as water or saline, on an unclean area of the body cavity. Furthermore, pathway fluid injector 314 (or a different tube, not shown) may be used for applying suction, in order to evacuate various liquids and/or solids which exist in the body cavity and interfere with the inspection.

Tip section 334 may further include therein a side-pointing camera 316 which may capture images through a hole in a cylindrical surface 305 of the tip section. A discrete side illuminator 322, which is optionally similar to discrete front illuminator 308, may be associated with front-pointing camera 304 and used for illuminating its field of view through another hole in cylindrical surface 305. In a different configuration (not shown), two or more discrete side illuminators may be present in the tip section, such as for supplying overall stronger illumination and/or for increasing the angular coverage of the illumination. These two or more discrete side illuminators may be located next to one another so that they share a same protective window on the cylindrical surface of the tip section.

A side fluid injector 320 may be used for cleaning at least one of side-pointing camera 316 and discrete side illuminator 322. In order to prevent tissue damage when cylindrical surface 305 of tip section 334 contacts a side wall of the body cavity, side fluid injector 320 and side-pointing camera 316 may be located in a depression 318 in the cylindrical surface. This way, side fluid injector 320 may be elevated from depression 318 but still not significantly protrude from the level of cylindrical surface 305. The elevation of side fluid injector 320 may enable it to inject fluid, from its side 320a, onto side-pointing camera 316. In an alternative configuration (not shown), one or more discrete side illuminators may also be included in the depression, so that fluid injected from the side fluid injector may reach them. In yet another configuration (not shown), a side-pointing camera, one or more side illuminators and a side fluid injector may not be located in a depression, but rather be on essentially the same level as the cylindrical surface of the tip section 334.

Figure 4:
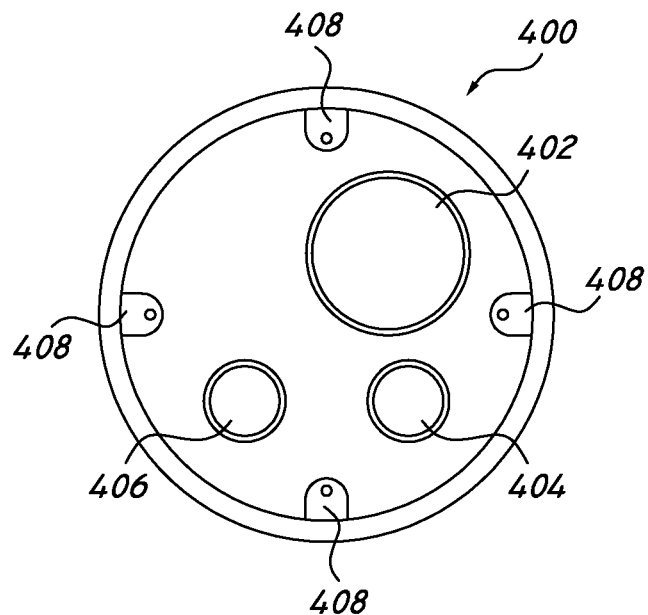
FIG. 4 shows a cross-sectional view of a bending section of a multi-camera endoscope, according to some embodiments.

Reference is now made to FIG. 4, which shows a cross-sectional view of a bending section 400 of a multi-camera endoscope, such as multi-camera endoscope 300 of FIG. 3. A plurality of steering cable eyes, such as four eyes 408, are positioned on the internal walls of bending section 400. Through these eyes 408, steering cables are threaded, to enable the maneuvering of bending section 400. Bending section 400 may also include a working channel 402, through which surgical tools may be inserted, a fluid channel 406, through which fluids and/or liquids may be infused, and an electrical channel 404, through which a plurality of electrical cables may be threaded, for transmitting video signals from the cameras and for supplying power to the cameras and the discrete illuminators.

For simplicity of presentation, FIG. 4 only shows a single working channel 402, although in a different configuration (not shown), more than one working channel may exist, to enable the insertion of multiple surgical tools simultaneously. Similarly, only one fluid channel 406 is shown, although in a different configuration (not shown) more than one fluid channel may be used, such as for separately feeding at least one of a front fluid injector, a side fluid injector and/or a pathway fluid injector, as well as for separately providing suction through the pathway fluid injector. Additionally, FIG. 4 shows only a single electrical channel 404, but in other configurations (not shown), one or more of the electrical cables threaded through the elongated shaft and/or the bending section may be separated into a plurality of tubes, for example in order to distance cables causing magnetic induction from cables which may be influenced by this phenomena.

Figure 5:
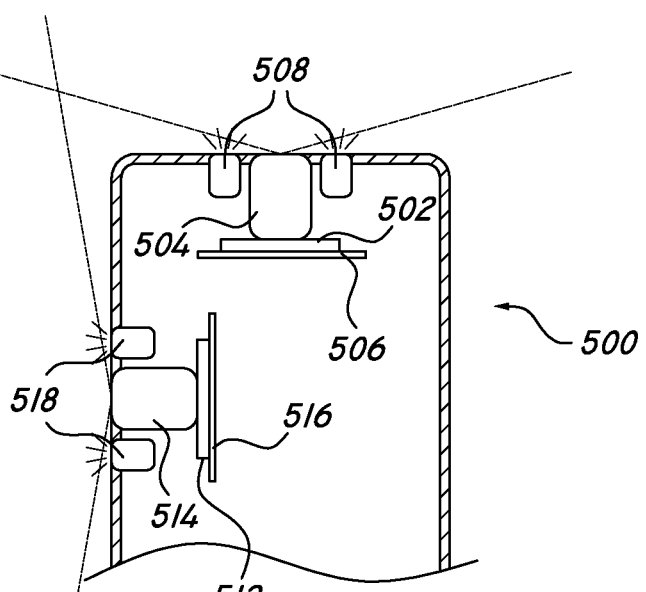
FIG. 5 shows a cross-sectional view of a tip section of a multi-camera endoscope, according to some embodiments.

Reference is now made to FIG. 5, which shows a cross-sectional view of a tip section 500 of a multi-camera endoscope, according to an embodiment. Tip section 500 may include a front-pointing image sensor 502, such as Charge Coupled Device (CCD) or a Complementary Metal Oxide Semiconductor (CMOS) image sensor. Front-pointing image sensor 502 may be mounted on an integrated circuit board 506, which may be rigid or flexible. Integrated circuit board 506 may supply front-pointing image sensor 502 with the necessary electrical power, and may derive still images and/or video feeds captured by the image sensor. Integrated circuit board 506 may be connected to a set of electrical cables (not shown) which may be threaded through an electrical channel running through the elongated shaft of the endoscope. Front-pointing image sensor 502 may have a lens assembly 504 mounted on top of it and providing the necessary optics for receiving images. Lens assembly 504 may include a plurality of lenses, static or movable, which may provide a field of view of at least 90 degrees and up to essentially 180 degrees. Lens assembly 504 may provide a focal length of about 3 to 100 millimeters. Front-pointing image sensor 502 and lens assembly 504, with or without integrated circuit board 506, may be jointly referred to as a "front pointing camera".

One or more discrete front illuminators 508 may be placed next to lens assembly 504, for illuminating its field of view. Optionally, discrete front illuminators 508 may be attached to the same integrated circuit board 506 on which front-pointing image sensor 502 is mounted (this configuration is not shown).

Tip section 500 may include a side-pointing image sensor 512, such as Charge Coupled Device (CCD) or a Complementary Metal Oxide Semiconductor (CMOS) image sensor. Front-pointing image sensor 502 may be mounted on an integrated circuit board 516, which may be rigid or flexible. Integrated circuit board 516 may supply side-pointing image sensor 512 with the necessary electrical power, and may derive still images and/or video feeds captured by the image sensor. Integrated circuit board 516 may be connected to a set of electrical cables (not shown) which may be threaded through an electrical channel running through the elongated shaft of the endoscope.

Side-pointing image sensor 512 may have a lens assembly 514 mounted on top of it and providing the necessary optics for receiving images. Lens assembly 514 may include a plurality of lenses, static or movable, which may provide a field of view of at least 90 degrees and up to essentially 180 degrees. Lens assembly 514 may provide a focal length of about 2 to 33 millimeters. Side-pointing image sensor 512 and lens assembly 514, with or without integrated circuit board 516, may be jointly referred to as a "side pointing camera".

One or more discrete side illuminators 518 may be placed next to lens assembly 514, for illuminating its field of view. Optionally, discrete front illuminators 518 may be attached to the same integrated circuit board 516 on which side-pointing image sensor 512 is mounted (this configuration is not shown).

In another configuration (not shown), integrated circuit boards 506 and 516 may be a single integrated circuit board on which both front and side-pointing image sensors 502 and 512 are mounted. For this purpose, the integrated circuit board may be essentially L-shaped.

Front and side-pointing image sensors 502 and 512 may be similar or identical in terms of, for example, field of view, resolution, light sensitivity, pixel size, focal length, focal distance and/or the like.

Optionally, side-pointing image sensor 512 and lens assembly 514 are advantageously positioned relatively close to the distal end surface of tip section 500. For example, a center of the side-pointing camera (which is the center axis of side-pointing image sensor 512 and lens assembly 514) is positioned approximately 7 to 11 millimeters from the distal end of the tip section. This is enabled by an advantageous miniaturizing of the front and side-pointing cameras, which allows for enough internal space in the tip section for angular positioning of the cameras without colliding.

Figure 6:
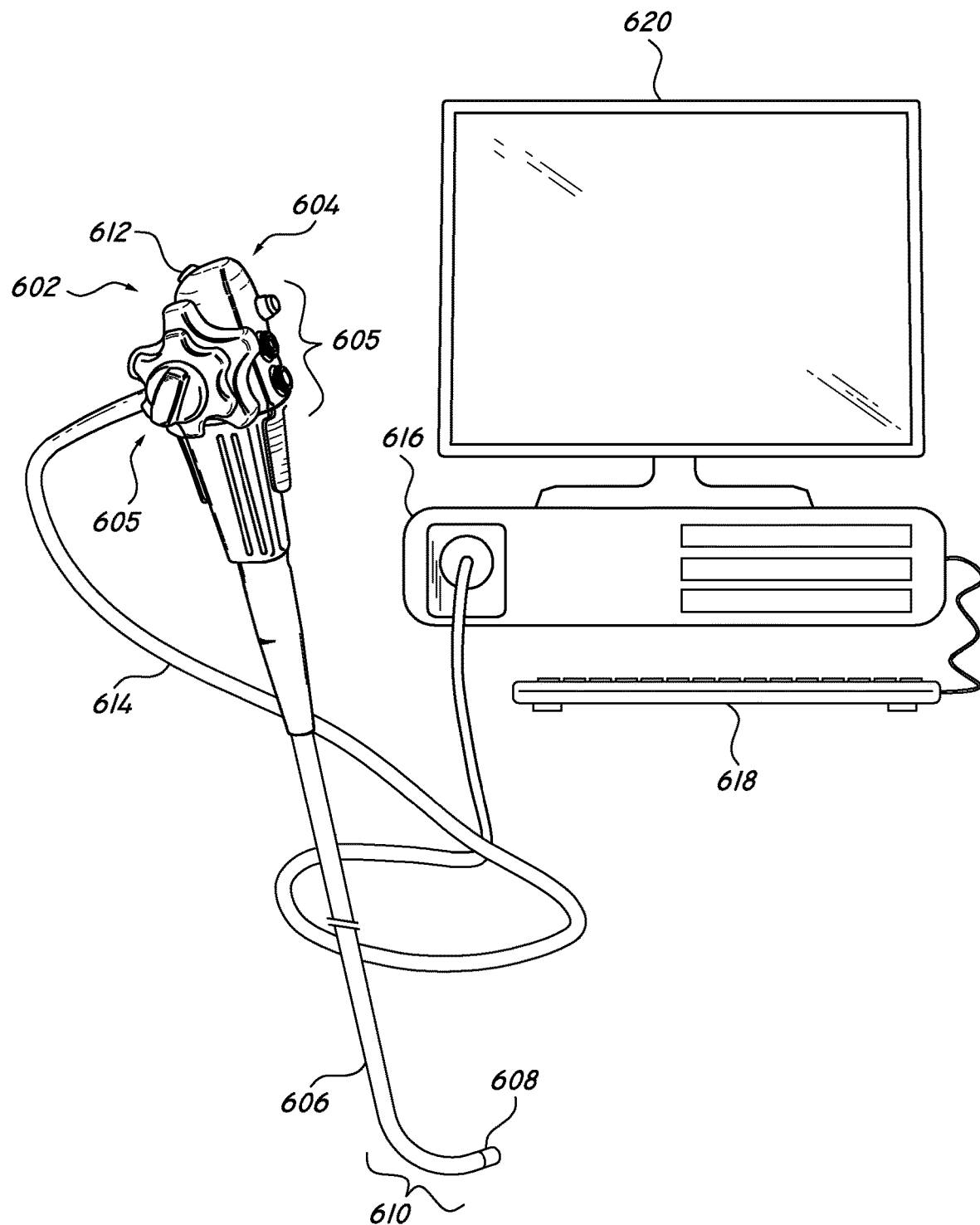
FIG. 6 shows a semi-pictorial view of a multi-camera endoscopy system, according to some embodiments.
Figure 7A:
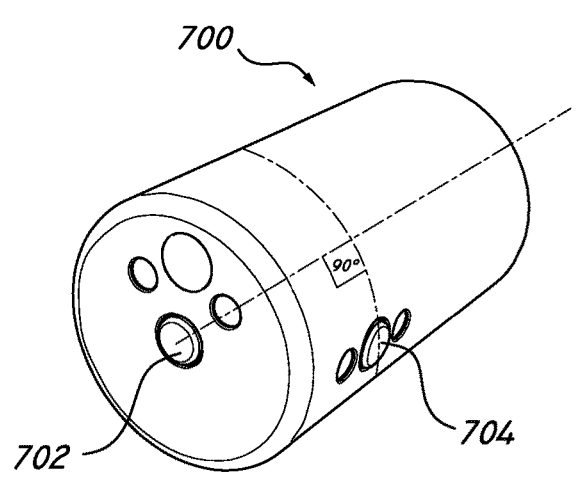
FIGS. 7A-D show perspective views of multiple tip section configurations, according to some embodiments.
Figure 7B:
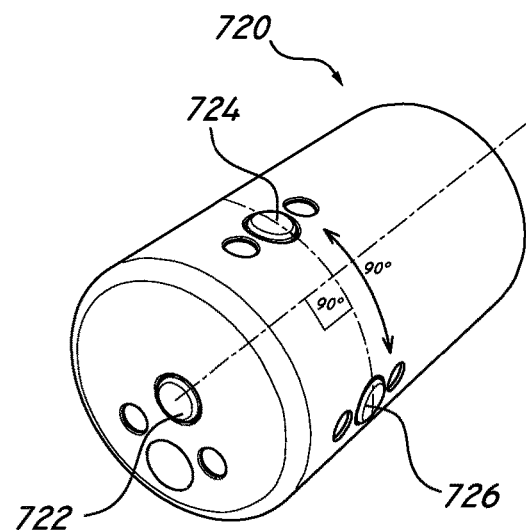
Figure 7C:
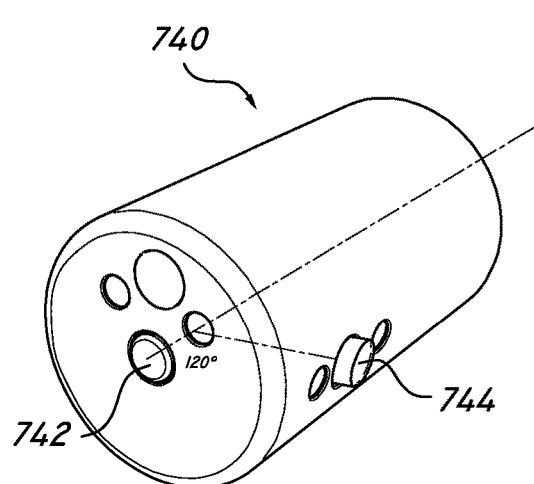
Figure 7D:
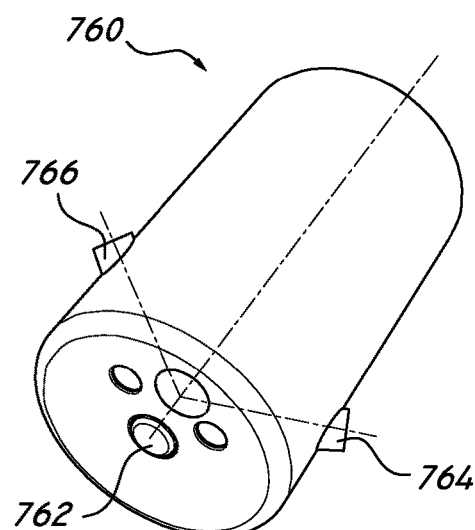

Reference is now made to FIG. 6, which shows a semi-pictorial view multi-camera endoscopy system 600. System 600 may include a multi-camera endoscope 602, such as the endoscope of FIGS. 2, 3, 4 and/or 5. Multi-camera endoscope 602 may include a handle 604, from which an elongated shaft 606 emerges. Elongated shaft 606 terminates with a tip section 608 which is turnable by way of a bending section 610. Handle 604 may be used for maneuvering elongated shaft 606 within a body cavity; the handle may include one or more knobs and/or switches 605 which control bending section 610 as well as functions such as fluid injection and suction. Handle 604 may further include a working channel opening 612 through which surgical tools may be inserted.

A utility cable 614 may connect between handle 604 and a controller 616. Utility cable 614 may include therein one or more fluid channels and one or more electrical channels. The electrical channel(s) may include at least one data cable for receiving video signals from the front and side-pointing cameras, as well as at least one power cable for providing electrical power to the cameras and to the discrete illuminators.

Controller 616 may govern power transmission to the endoscope's 602 tip section 608, such as for the tip section's cameras and illuminators. Controller 616 may further control one or more fluid, liquid and/or suction pump which supply corresponding functionalities to endoscope 602. One or more input devices, such as a keyboard 618, may be connected to controller 616 for the purpose of human interaction with the controller. In another configuration (not shown), an input device, such as a keyboard, may be integrated with the controller in a same casing.

A display 620 may be connected to controller 616, and configured to display images and/or video streams received from the cameras of multi-camera endoscope 602. Display 620 may further be operative to display a user interface for allowing a human operator to set various features of system 600.

Optionally, the video streams received from the different cameras of multi-camera endoscope 602 may be displayed separately on display 620, either side-by-side or interchangeably (namely, the operator may switch between views from the different cameras manually). Alternatively, these video streams may be processed by controller 616 to combine them into a single, panoramic video frame, based on an overlap between fields of view of the cameras.

In another configuration (not shown), two or more displays may be connected to controller 616, each for displaying a video stream from a different camera of the multi-camera endoscope.

Reference is now made to FIGS. 7A-D, in which multiple configurations 700, 720, 740 and 760 of a tip section are shown.

In configuration 700, a front-pointing camera 702 and a side-pointing camera 704 are essentially perpendicular to one another, and have, correspondingly, perpendicular fields of view.

In configuration 720, a front-pointing camera 722 is essentially perpendicular to a first side-pointing camera 724 and a second side-pointing camera 726. First and second side-pointing cameras 724-726 are pointing perpendicularly to one another, and are positioned essentially 90 degrees apart in the cylindrical surface of the tip section. In another configuration (not shown), a first and a second side-pointing cameras may be positioned more than 90 degrees apart in the cylindrical surface of the tip section, such as 120-150 degrees apart or 150-180 degrees apart. For example, the first and second side-pointing cameras may be positioned in 180 degrees apart, in opposite sides of the cylindrical surface of the tip section, so that they point in opposite directions. In yet further configurations (not shown), three or more side-pointing cameras may be positioned in the cylindrical surface of the tip section, for example, three cameras having 120 degrees in between them.

In configuration 740, a side-pointing camera 744 is pointing slightly backwards, so that it forms an angle larger than 90 degrees relative to a front-pointing camera 742. As an example, an angle of 120 degrees is shown. In another configuration (not shown), the angle is 100-145 degrees.

In configuration 760, two opposing side cameras 764 and 766 are shown, which are pointing slightly backwards, so that they each form an angle larger than 90 degrees relative to a front-pointing camera 762. As an example, an angle of 120 degrees is shown. In another configuration (not shown), the angle is 100-145 degrees.

Similarly, in other configurations (not shown), three or more side-pointing cameras may be positioned in the cylindrical surface of the tip section, each pointing slightly backwards and having an certain angle in between; in the case of three cameras, they may have an angle of 120 degrees in between them.

Figure 8:
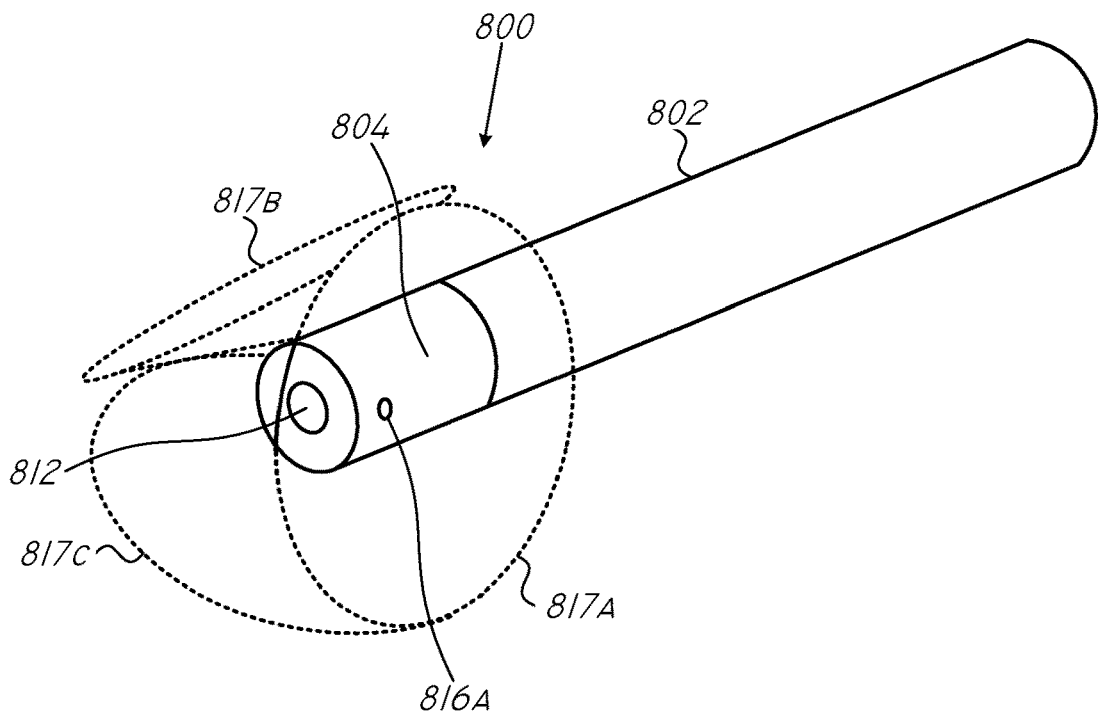
FIG. 8 shows a perspective view of a multi-camera endoscope, according to some embodiments.

Reference is now made to FIG. 8, which shows a perspective view of a multi-camera endoscope, according to some embodiments. Endoscope 800 includes an elongated shaft 802 which typically includes a bending section (not shown) and a tip section 804 which terminates the endoscope. Tip section 804 includes three side-pointing cameras 816a, 816b (not shown) and 816c (not shown). Discrete side illuminators (for example LEDs), not shown, may be associated with the side-pointing cameras 816a-c for illuminating their respective fields of view 817a-c. Tip section 804 includes further includes a working channel 812 which may be a hollow opening configured for insertion of a surgical tool to operate on various tissues. For example, miniature forceps may be inserted through working channel 812 in order to remove a polyp or sample of which for biopsy.

Tip 804 may further include other elements/components, (for example, as described herein according to various embodiments) such as fluid injector(s) for cleaning the cameras and/or there illuminators and pathway fluid injector(s) for inflating and/or cleaning the body cavity into which endoscope 800 is inserted.

Figure 9:
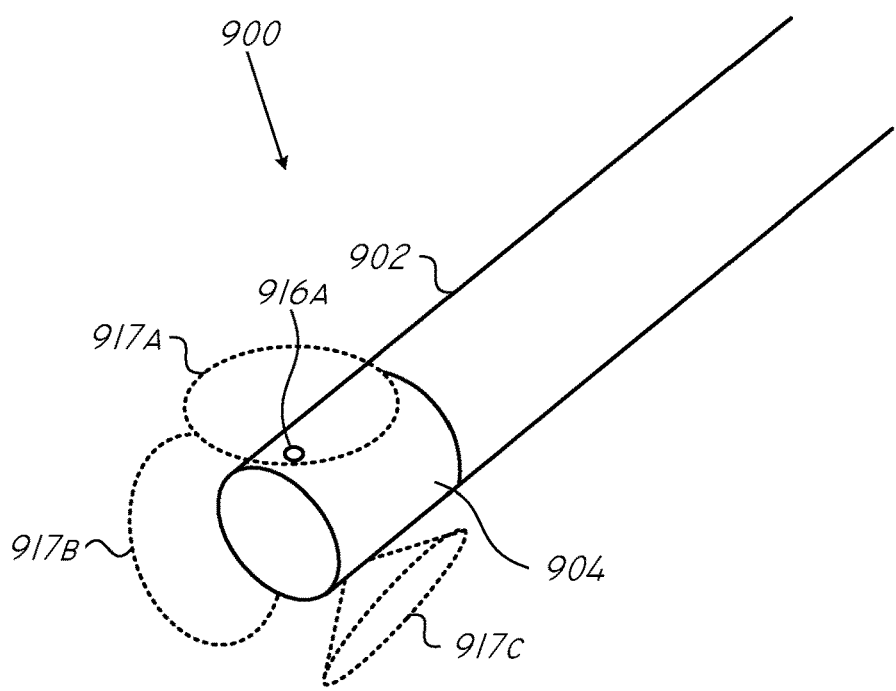
FIG. 9 shows a perspective view of a multi-camera endoscope, according to some embodiments.

Reference is now made to FIG. 9, which shows a perspective view of a multi-camera endoscope, according to some embodiments. Endoscope 900 is similar to endoscope 800 how ever does not include a working channel. Elongated shaft 902, tip section 904, side-pointing cameras 916a, 916b (not shown) and 916c (not shown), and their respective fields of view 917a-c may be similar to elongated shaft 802, tip section 804, side-pointing cameras 816a, 816b (not shown) and 816c (not shown), and their respective fields of view 817a-c of endoscope 800.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

I claim:

1. A tip section of a multi-camera endoscope, the tip section having a cylindrical surface and a distal end having a planar surface perpendicular to said cylindrical surface, comprising:
    a front-pointing camera, wherein the front-pointing camera comprises a lens assembly providing a front field of view of at least 120 degrees and a focal length of approximately 3-100 millimeters, wherein the front-pointing camera is positioned on the planar surface of the distal end of the tip section;
    two side-pointing cameras each having a center positioned approximately 7 to 11 millimeters from the planar surface of the distal end, wherein each of said two side-pointing cameras has a side field of view of at least 120 degrees, has a focal length of approximately 2-33 millimeters, is positioned on said cylindrical surface and has a discrete illuminator associated therewith, wherein the side field of view provided by said two side-pointing cameras partially overlaps with the front field of view such that an object of interest viewed by said one of said two side-pointing cameras remains in the side field of view of said side-pointing camera while said tip section is being turned towards the object and at least until the object becomes visible in the front field of view;
    a working channel configured for insertion of a surgical tool; and
    a pathway fluid injector for inflating and/or cleaning a body cavity into which the endoscope is inserted.

2. The tip section according to claim 1, further comprising two or more side fluid injectors configured for cleaning said two side-pointing cameras and/or said discrete side illuminators wherein each of said two or more side fluid injectors is positioned on said cylindrical surface.

3. The tip section according to claim 1, wherein said two side-pointing cameras are pointing at directions essentially opposing to one another.

4. The tip section according to claim 1, comprising three or more side-pointing cameras positioned essentially at equal distances from each other along the perimeter of said tip section.

5. The tip section according to claim 1, wherein each of said illuminators comprises a light-emitting diode (LED) and wherein each of said illuminators is positioned on said cylindrical surface.

6. A multi-camera endoscope comprising an elongated shaft terminating with a tip section turnable by way of a bending section, wherein said tip section has a cylindrical surface and a distal end having a planar surface perpendicular to said cylindrical surface, and comprises:
    a front-pointing camera, wherein the front-pointing camera comprises a lens assembly providing a front field of view of at least 120 degrees and a focal length of approximately 3-100 millimeters, wherein the front-pointing camera is positioned on the planar surface of the distal end of the tip section;
    two side-pointing cameras each having a center positioned approximately 7 to 11 millimeters from the planar surface of the distal end, wherein each of said two or more side-pointing cameras has a side field of view of at least 120 degrees, has a focal length of approximately 2-33 millimeters, is positioned on said cylindrical surface and has a discrete illuminator associated therewith, wherein the side field of view provided by said two side-pointing cameras partially overlaps with the front field of view such that an object of interest viewed by said one of said two side-pointing cameras remains in the side field of view of said side-pointing camera while said tip section is being turned towards the object and at least until the object becomes visible in the front field of view;
    a working channel configured for insertion of a surgical tool; and
    a pathway fluid injector for inflating and/or cleaning a body cavity into which the endoscope is inserted.

7. The multi-camera endoscope according to claim 6, wherein said tip section further comprises two or more side fluid injectors configured for cleaning said two side-pointing cameras and/or said discrete side illuminators and wherein each of said two or more side fluid injectors is positioned on said cylindrical surface.

8. The multi-camera endoscope according to claim 6, wherein said two side-pointing cameras are pointing at directions essentially opposing to one another.

9. The tip section according to claim 6, wherein said tip section comprises three or more side-pointing cameras positioned essentially at equal distances from each other along the perimeter of said tip section.

* * * * *